(12) United States Patent
Winston et al.

(10) Patent No.: US 11,517,718 B2
(45) Date of Patent: *Dec. 6, 2022

(54) APPARATUS FOR THE INTRODUCTION AND MANIPULATION OF MULTIPLE TELESCOPING CATHETERS

(71) Applicant: Edwards Lifesciences Corporation, Irvine, CA (US)

(72) Inventors: Matthew T. Winston, Aliso Viejo, CA (US); Christopher J. Olson, Lake Forest, CA (US); Asher L. Metchik, Rolling Hills Estates, CA (US); Tri D. Tran, Fountain Valley, CA (US); Alexander J. Siegel, Irvine, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 202 days.

This patent is subject to a terminal disclaimer.

(21) Appl. No.: 16/870,790

(22) Filed: May 8, 2020

(65) Prior Publication Data

US 2020/0269017 A1 Aug. 27, 2020

Related U.S. Application Data

(63) Continuation of application No. 15/796,436, filed on Oct. 27, 2017, now Pat. No. 10,653,862.
(Continued)

(51) Int. Cl.
*A61M 25/01* (2006.01)
*A61F 2/24* (2006.01)
(Continued)

(52) U.S. Cl.
CPC ....... *A61M 25/0147* (2013.01); *A61F 2/2427* (2013.01); *A61F 2/2436* (2013.01);
(Continued)

(58) Field of Classification Search
CPC .... A61F 2/2427; A61F 2/2433; A61F 2/2436; A61M 25/0147; A61M 25/0662;
(Continued)

(56) References Cited

U.S. PATENT DOCUMENTS 3,874,388 A 4/1975 King et al.
4,340,091 A 7/1982 Skelton et al.
(Continued)

FOREIGN PATENT DOCUMENTS

CN 1142351 A 2/1997
CN 103071230 A 5/2013
(Continued)

OTHER PUBLICATIONS

Al Zaibag et al., "Percutaneous Ballon Valvotomy in Tricuspid Stenosis", British Heart Journal, vol. 57, No. 1, Jan. 1987.
(Continued)

*Primary Examiner* — Ryan J. Severson
(74) *Attorney, Agent, or Firm* — Thomas C. Richardson

(57) ABSTRACT

A delivery apparatus includes a steerable shaft having a pull-wire conduit. A pull wire extends through the pull-wire conduit. The steerable shaft includes one or more layers. A compression-resistance portion is incorporated into at least one of the one or more layers. A cross-section of the compression-resistance portion has an arcuate shape that extends along a portion of a cross-section of the steerable shaft. The compression-resistance portion has a hardness that is greater than a hardness of the one or more layers that the compression-resistance portion is incorporated into.

25 Claims, 7 Drawing Sheets

Related U.S. Application Data

(60) Provisional application No. 62/418,528, filed on Nov. 7, 2016.

(51) Int. Cl.
*A61M 25/06* (2006.01)
*A61M 25/00* (2006.01)

(52) U.S. Cl.
CPC ....... *A61M 25/0662* (2013.01); *A61F 2/2433* (2013.01); *A61M 25/005* (2013.01); *A61M 2025/015* (2013.01)

(58) Field of Classification Search
CPC ............ A61M 25/005; A61M 25/0133; A61M 25/0144; A61M 2025/015; A61B 2017/003; A61B 2017/00305; A61B 2017/00318; A61B 2017/00323; A61B 2017/00336
See application file for complete search history.

(56) References Cited

U.S. PATENT DOCUMENTS

| | | | |
|---|---|---|---|
| 4,506,669 A | 3/1985 | Blake, III | |
| 4,590,937 A | 5/1986 | Deniega | |
| 4,693,248 A | 9/1987 | Failla | |
| 4,803,983 A | 2/1989 | Siegel | |
| 5,125,895 A | 6/1992 | Buchbinder et al. | |
| 5,171,252 A | 12/1992 | Friedland | |
| 5,195,962 A | 3/1993 | Martin et al. | |
| 5,292,326 A | 3/1994 | Green et al. | |
| 5,327,905 A | 7/1994 | Avitall | |
| 5,345,937 A * | 9/1994 | Middleman ........ A61M 25/0147 | |
| | | | 604/95.01 |
| 5,363,861 A | 11/1994 | Edwards et al. | |
| 5,368,564 A * | 11/1994 | Savage ............. A61M 25/0147 | |
| | | | 604/95.04 |
| 5,370,685 A | 12/1994 | Stevens | |
| 5,389,077 A | 2/1995 | Melinyshyn et al. | |
| 5,411,552 A | 5/1995 | Andersen et al. | |
| 5,450,860 A | 9/1995 | O'Connor | |
| 5,456,674 A | 10/1995 | Bos et al. | |
| 5,474,057 A | 12/1995 | Makower et al. | |
| 5,478,353 A | 12/1995 | Yoon | |
| 5,487,746 A | 1/1996 | Yu et al. | |
| 5,507,725 A * | 4/1996 | Savage ............. A61M 25/0147 | |
| | | | 604/95.04 |
| 5,565,004 A | 10/1996 | Christoudias | |
| 5,607,462 A | 3/1997 | Imran | |
| 5,609,598 A | 3/1997 | Laufer et al. | |
| 5,611,794 A | 3/1997 | Sauer et al. | |
| 5,626,607 A | 5/1997 | Malecki et al. | |
| 5,695,504 A | 12/1997 | Gifford, III et al. | |
| 5,716,417 A | 2/1998 | Girard et al. | |
| 5,727,569 A | 3/1998 | Benetti et al. | |
| 5,741,297 A | 4/1998 | Simon | |
| 5,782,746 A | 7/1998 | Wright | |
| 5,797,960 A | 8/1998 | Stevens et al. | |
| 5,836,311 A | 11/1998 | Borst et al. | |
| 5,843,076 A | 12/1998 | Webster, Jr. et al. | |
| 5,855,590 A | 1/1999 | Malecki et al. | |
| 5,885,271 A | 3/1999 | Hamilton et al. | |
| 5,888,247 A | 3/1999 | Benetti | |
| 5,891,017 A | 4/1999 | Swindle et al. | |
| 5,891,112 A | 4/1999 | Samson | |
| 5,894,843 A | 4/1999 | Benetti et al. | |
| 5,921,979 A | 7/1999 | Kovac et al. | |
| 5,944,738 A | 8/1999 | Amplatz et al. | |
| 5,957,835 A | 9/1999 | Anderson et al. | |
| 5,972,020 A | 10/1999 | Carpentier et al. | |
| 5,980,534 A | 11/1999 | Gimpelson | |
| 6,004,329 A | 12/1999 | Myers | |
| 6,010,531 A | 1/2000 | Donlon et al. | |
| 6,017,358 A | 1/2000 | Yoon et al. | |
| 6,086,600 A | 7/2000 | Kortenbach | |
| 6,120,496 A | 9/2000 | Whayne et al. | |
| 6,132,370 A | 10/2000 | Furnish et al. | |
| 6,162,239 A | 12/2000 | Manhes | |
| 6,165,183 A | 12/2000 | Kuehn et al. | |
| 6,171,295 B1 * | 1/2001 | Garabedian ........ A61M 25/005 |
| | | | 604/524 |
| 6,182,664 B1 | 2/2001 | Cosgrove | |
| 6,193,732 B1 | 2/2001 | Frantzen et al. | |
| 6,193,734 B1 | 2/2001 | Bolduc et al. | |
| 6,200,315 B1 | 3/2001 | Gaiser et al. | |
| 6,228,032 B1 | 5/2001 | Eaton et al. | |
| 6,241,743 B1 | 6/2001 | Levin et al. | |
| 6,269,819 B1 | 8/2001 | Oz et al. | |
| 6,269,829 B1 | 8/2001 | Chen et al. | |
| 6,312,447 B1 | 11/2001 | Grimes | |
| 6,461,366 B1 | 10/2002 | Seguin | |
| 6,468,285 B1 | 10/2002 | Hsu et al. | |
| 6,508,805 B1 * | 1/2003 | Garabedian ........ A61M 25/005 |
| | | | 604/524 |
| 6,508,806 B1 | 1/2003 | Hoste | |
| 6,508,825 B1 | 1/2003 | Selmon et al. | |
| 6,530,933 B1 | 3/2003 | Yeung et al. | |
| 6,537,290 B2 | 3/2003 | Adams et al. | |
| 6,544,215 B1 | 4/2003 | Bencini et al. | |
| 6,626,930 B1 | 9/2003 | Allen et al. | |
| 6,629,534 B1 | 10/2003 | St. Goar et al. | |
| 6,709,429 B1 * | 3/2004 | Schaefer ................ D04C 1/06 |
| | | | 604/524 |
| 6,719,767 B1 | 4/2004 | Kimblad | |
| 6,764,510 B2 | 7/2004 | Vidlund et al. | |
| 6,770,083 B2 | 8/2004 | Seguin | |
| 6,837,867 B2 | 1/2005 | Kortelling | |
| 6,855,137 B2 | 2/2005 | Bon | |
| 6,866,660 B2 * | 3/2005 | Garabedian ........ A61M 25/005 |
| | | | 604/524 |
| 6,913,614 B2 | 7/2005 | Marino et al. | |
| 6,939,337 B2 | 9/2005 | Parker et al. | |
| 6,942,654 B1 * | 9/2005 | Schaefer ............ A61M 25/005 |
| | | | 623/1.13 |
| 6,945,956 B2 | 9/2005 | Waldhauser et al. | |
| 7,048,754 B2 | 5/2006 | Martin et al. | |
| 7,101,395 B2 | 9/2006 | Tremulis et al. | |
| 7,125,421 B2 | 10/2006 | Tremulis et al. | |
| 7,288,097 B2 | 10/2007 | Seguin | |
| 7,371,210 B2 | 5/2008 | Brock et al. | |
| 7,464,712 B2 | 12/2008 | Oz et al. | |
| 7,509,959 B2 | 3/2009 | Oz et al. | |
| 7,569,062 B1 | 8/2009 | Kuehn et al. | |
| 7,618,449 B2 | 11/2009 | Tremulis et al. | |
| 7,682,369 B2 | 3/2010 | Seguin | |
| 7,731,706 B2 | 6/2010 | Potter | |
| 7,744,609 B2 | 6/2010 | Allen et al. | |
| 7,748,389 B2 | 7/2010 | Salahieh et al. | |
| 7,753,932 B2 | 7/2010 | Gingrich et al. | |
| 7,758,596 B2 | 7/2010 | Oz et al. | |
| 7,780,723 B2 | 8/2010 | Taylor | |
| 7,803,185 B2 | 9/2010 | Gabbay | |
| 7,824,443 B2 | 11/2010 | Salahieh et al. | |
| 7,981,123 B2 | 7/2011 | Seguin | |
| 7,985,214 B2 * | 7/2011 | Garabedian ........ A61M 25/005 |
| | | | 604/533 |
| 7,988,724 B2 | 8/2011 | Salahieh et al. | |
| 8,052,750 B2 | 11/2011 | Tuval et al. | |
| 8,070,805 B2 | 12/2011 | Vidlund et al. | |
| 8,096,985 B2 | 1/2012 | Legaspi et al. | |
| 8,104,149 B1 | 1/2012 | McGarity | |
| 8,133,239 B2 | 3/2012 | Oz et al. | |
| 8,147,542 B2 | 4/2012 | Maisano et al. | |
| 8,172,856 B2 | 5/2012 | Eigler et al. | |
| 8,206,437 B2 | 6/2012 | Bonhoeffer et al. | |
| 8,216,301 B2 | 7/2012 | Bonhoeffer et al. | |
| 8,303,653 B2 | 11/2012 | Bonhoeffer et al. | |
| 8,313,525 B2 | 11/2012 | Tuval et al. | |
| 8,323,241 B2 * | 12/2012 | Salahieh ........... A61M 25/0138 |
| | | | 604/95.04 |
| 8,348,995 B2 | 1/2013 | Tuval et al. | |
| 8,348,996 B2 | 1/2013 | Tuval et al. | |
| 8,414,643 B2 | 4/2013 | Tuval et al. | |

(56) References Cited

U.S. PATENT DOCUMENTS

| | | | |
|---|---|---|---|
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,568,472 B2* | 10/2013 | Marchand | A61F 2/2436 623/2.11 |
| 8,579,965 B2 | 11/2013 | Bonhoeffer et al. |
| 8,585,756 B2 | 11/2013 | Bonhoeffer et al. |
| 8,608,736 B2* | 12/2013 | Kaufmann | A61M 25/0144 606/41 |
| 8,652,202 B2 | 2/2014 | Alon et al. |
| 8,668,733 B2 | 3/2014 | Haug et al. |
| 8,708,953 B2* | 4/2014 | Salahieh | A61M 25/0045 604/95.01 |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,920,369 B2* | 12/2014 | Salahieh | A61B 17/00234 604/95.04 |
| 8,945,177 B2 | 2/2015 | Dell et al. |
| 9,034,032 B2 | 5/2015 | McLean et al. |
| 9,061,119 B2* | 6/2015 | Le | A61M 25/0147 |
| 9,155,619 B2* | 10/2015 | Liu | A61F 2/2427 |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,339,384 B2* | 5/2016 | Tran | A61F 2/2433 |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,586,025 B2* | 3/2017 | Salahieh | A61M 25/0136 |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,913,717 B2* | 3/2018 | Chau | A61F 2/2463 |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,076,638 B2* | 9/2018 | Tran | A61F 2/2436 |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 10,653,862 B2* | 5/2020 | Winston | A61M 25/0147 |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0097119 A1* | 5/2003 | Garabedian | A61M 25/005 604/524 |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0004365 A1 | 1/2004 | Olsen |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122360 A1* | 6/2004 | Waldhauser | A61M 25/005 264/234 |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0162543 A1* | 8/2004 | Schaefer | D04C 1/06 604/524 |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0182388 A1* | 8/2005 | Garabedian | A61M 25/005 604/527 |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0005131 A1* | 1/2007 | Taylor | A61F 2/2433 623/2.11 |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065011 A1* | 3/2008 | Marchand | A61F 2/2433 604/103.05 |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |

(56) References Cited

U.S. PATENT DOCUMENTS

| | | |
|---|---|---|
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131865 A1 | 5/2009 | Partlett et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0281619 A1* | 11/2009 | Le .................. A61M 25/0147 623/2.11 |
| 2009/0287304 A1 | 11/2009 | Dahlgren et al. |
| 2010/0022823 A1 | 1/2010 | Goldfarb et al. |
| 2010/0049313 A1* | 2/2010 | Alon .................. A61F 2/2439 623/2.11 |
| 2010/0057037 A1 | 3/2010 | Webler |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2010/0331776 A1* | 12/2010 | Salahieh .................. A61M 25/0138 604/95.04 |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0282379 A1 | 11/2011 | Lee et al. |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0123327 A1 | 5/2012 | Miller |
| 2012/0209318 A1 | 8/2012 | Qadeer |
| 2012/0239142 A1* | 9/2012 | Liu .................. A61F 2/2436 623/2.11 |
| 2012/0277730 A1* | 11/2012 | Salahieh .................. A61B 1/00135 604/528 |
| 2012/0277853 A1 | 11/2012 | Rothstein |
| 2013/0030519 A1* | 1/2013 | Tran .................. A61F 2/958 623/2.11 |
| 2013/0035759 A1 | 2/2013 | Gross et al. |
| 2013/0041314 A1 | 2/2013 | Dillon |
| 2013/0046298 A1* | 2/2013 | Kaufman .................. A61M 25/0144 606/1 |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0116705 A1* | 5/2013 | Salahieh .................. A61M 25/0144 606/130 |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058324 A1* | 2/2014 | Salahieh .................. A61B 17/00234 604/95.04 |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0107623 A1* | 4/2014 | Salahieh .................. A61M 25/0105 604/528 |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0073341 A1* | 3/2015 | Salahieh .................. A61M 25/0013 604/95.01 |
| 2015/0094656 A1* | 4/2015 | Salahieh .................. A61M 25/0141 604/95.04 |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0136393 A1* | 5/2016 | Tsai .................. A61M 25/0136 604/95.04 |
| 2016/0155987 A1 | 6/2016 | Yoo et al. |
| 2016/0158497 A1* | 6/2016 | Tran .................. A61M 25/0147 604/95.04 |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100236 A1 | 4/2017 | Robertson et al. |
| 2017/0173303 A1* | 6/2017 | Salahieh .................. A61M 25/0147 |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |

(56) References Cited

U.S. PATENT DOCUMENTS

| | | |
|---|---|---|
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0269017 A1* | 8/2020 | Winston .............. A61F 2/2436 |
| 2020/0337842 A1 | 10/2020 | Metchik et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0307900 A1 | 10/2021 | Hacohen |
| 2021/0330456 A1 | 10/2021 | Hacohen et al. |
| 2021/0361422 A1 | 11/2021 | Gross et al. |
| 2021/0401434 A1 | 12/2021 | Tien et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |

FOREIGN PATENT DOCUMENTS

| | | |
|---|---|---|
| CN | 203663213 U | 6/2014 |
| CN | 106175845 A | 12/2016 |
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2012061657 A2 | 5/2012 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022052506 A1 | 3/2022 |
| WO | 2022068188 A1 | 4/2022 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

Batista RJ et al., "Partial left ventriculectomy to treat end-stage heart disease", Ann Thorac Surg., vol. 64, Issue—3, pp. 634-638, Sep. 1997.

Beall AC Jr. et al.,"Clinical experience with a dacron velour-covered teflon-disc mitral-valve prosthesis", Ann Thorac Surg., vol. 5, Issue 5, pp. 402-410, May 1968.

(56) References Cited

OTHER PUBLICATIONS

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et al., "Improved results with mitral valve repair using new surgical techniques", Eur J Cardiothorac Surg. 1995; Issue 9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device That Opens Clogged Arteries Gets a Failing Grade in a New Study", The New York Times, Jan. 3, 1991, pp. 1-2 [online], [retrieved on Jul. 29, 2009], Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et a., "Compassionate use of the PASCAL transcatheter mitral valve repair system for patients with severe mitral regurgitation: a multicentre, prospective, observational, first-in-man study," Lancet, vol. 390, pp. 773-780, 2017.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, vol. 13, No. 4, pp. 363-367, Dec. 1986.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vasc Interv Radiol 2003; 14:841-853.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Umaña JP et al., "'Bow-tie' mitral valve repair: an adjuvant technique for ischemic mitral regurgitation', Ann Thorac Surg., vol. 66, Issue—6, pp. 1640-1646, Nov. 1998.

Urban, Philip MD, "Coronary Artery Stenting", Editions Medecine et Hygiene, Geneve, pp. 1-47, 1991.

Watt et al., "Intravenous Adenosine in the Treatment, of Supraventricular Tachycardia: A Dose-Ranging Study and Interaction with Dipyridamole", Br. J. Clin. Pharmac, 21, pp. 227-230, 1986.

Wheatley, David J., "Valve Prosthesis", Rob & Smith's Operative Surgery, pp. 415-424, 1986.

\* cited by examiner

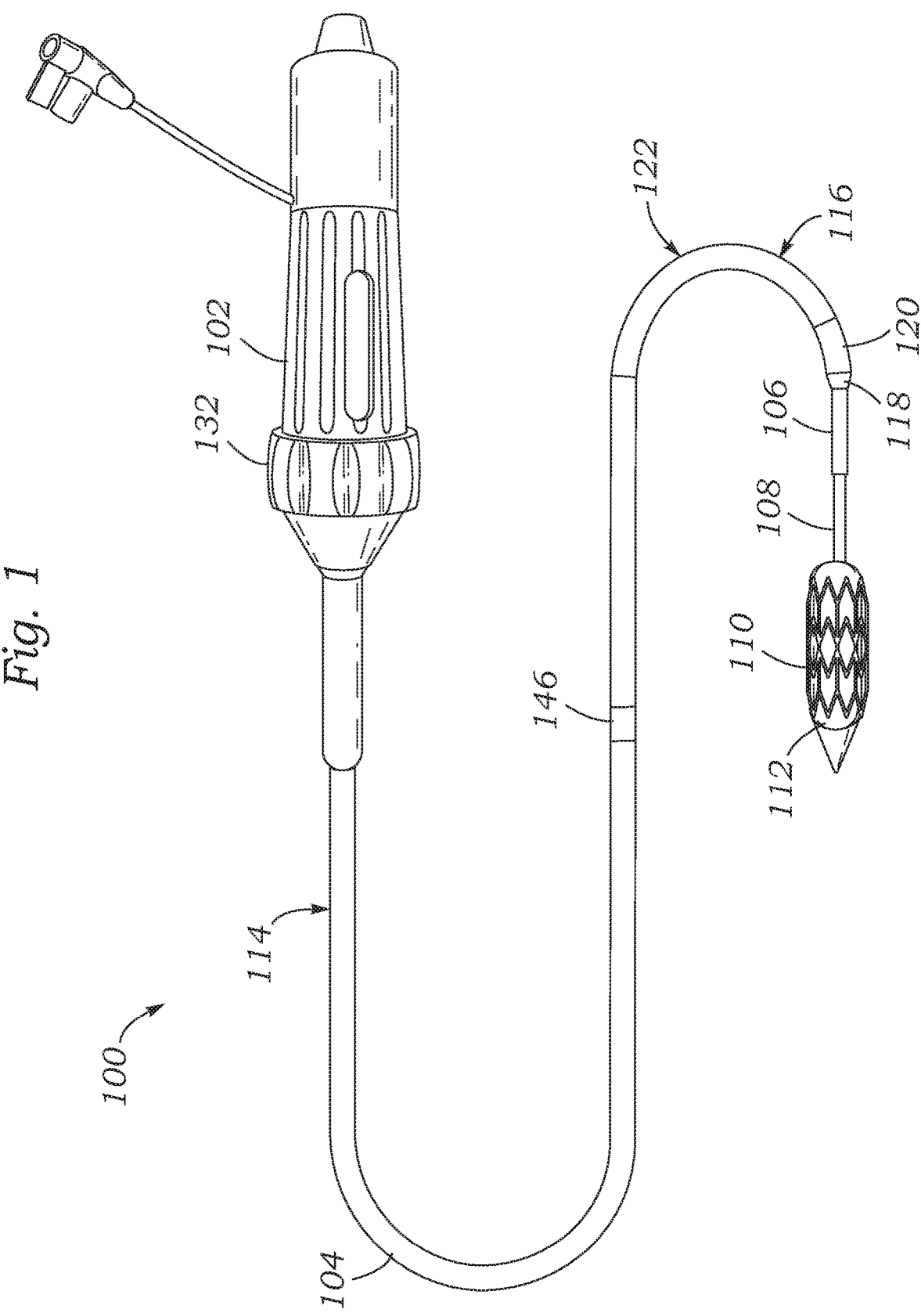

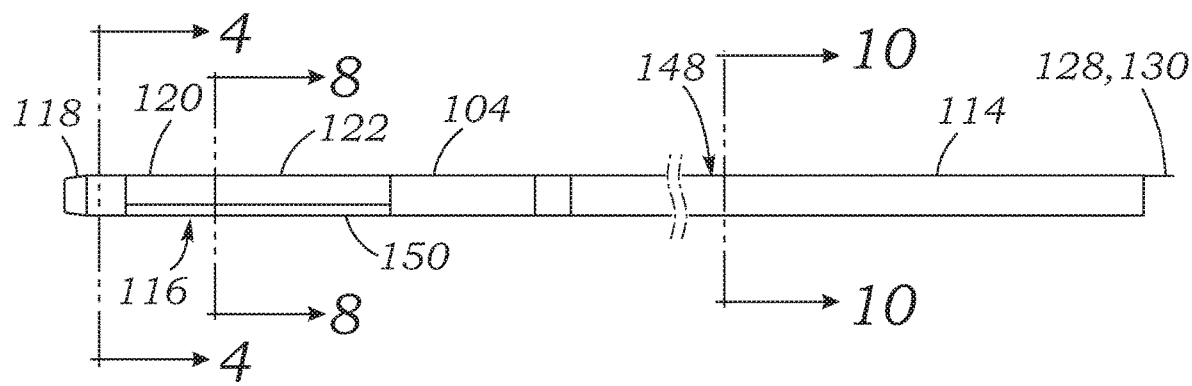
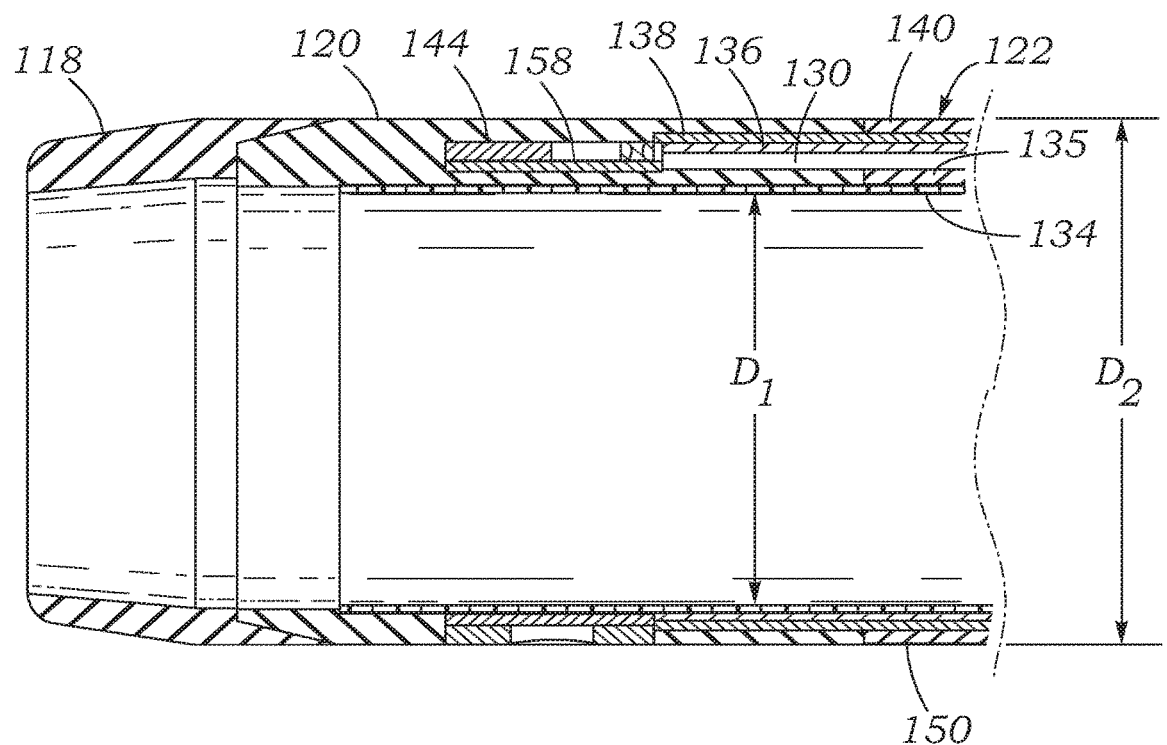

APPARATUS FOR THE INTRODUCTION AND MANIPULATION OF MULTIPLE TELESCOPING CATHETERS

CROSS REFERENCE TO RELATED APPLICATIONS

This application is a continuation of U.S. patent application Ser. No. 15/796,436, filed Oct. 27, 2017, which claims the benefit of U.S. Provisional Patent Application No. 62/418,528, filed Nov. 7, 2016, which are incorporated herein by reference in their entireties.

FIELD

The present application pertains to embodiments of steerable endovascular delivery devices.

BACKGROUND

Endovascular delivery devices are used in various procedures to deliver prosthetic medical devices or instruments to locations inside the body that are not readily accessible by surgery or where access without surgery is desirable. Access to a target location inside the body can be achieved by inserting and guiding the delivery device through a pathway or lumen in the body, including, but not limited to, a blood vessel, an esophagus, a trachea, any portion of the gastrointestinal tract, a lymphatic vessel, to name a few. In one specific example, a prosthetic heart valve can be mounted in a crimped state on the distal end of a delivery device and advanced through the patient's vasculature (e.g., through a femoral artery) until the prosthetic valve reaches the implantation site in the heart. The prosthetic valve is then expanded to its functional size such as by inflating a balloon on which the prosthetic valve is mounted, or by deploying the prosthetic valve from a sheath of the delivery device so that the prosthetic valve can self-expand to its functional size.

The usefulness of delivery devices is largely limited by the ability of the device to successfully navigate through small vessels and around tight bends in the vasculature, such as through the inferior vena cava or around the aortic arch. Various techniques have been employed to adjust the curvature of a section of a delivery device to help "steer" the valve through bends in the vasculature. Typically, a delivery device employs a pull wire having a distal end fixedly secured to the steerable section and a proximal end operatively connected to an adjustment knob located on a handle of the delivery device outside the body. The pull wire is typically disposed in a pull-wire lumen that extends longitudinally in or adjacent to a wall of the delivery device, for example, a sheath or catheter. Adjusting the adjustment knob, for example, rotating the knob, applies a pulling force on the pull wire, which in turn causes the steerable section to bend.

A drawback of many guide sheaths is that they are prone to undesirable deformation when deflected or flexed. For example, a guide sheath subject to significant curvature, such as when accessing the mitral valve in a transseptal approach, may kink at one or more locations along the radius of curvature, dramatically reducing the inner diameter of the guide sheath and resulting in unpredictable movement of the distal end of the guide sheath. A flexed guide sheath may also "pancake," in which the cross-section of the catheter is ovalized due to a lack of adherence between the materials of adjacent layers of the sheath. Additionally, a flexed guide sheath may be reduced in length, or foreshortened, due to axial compression of the shaft as it is flexed. Such deformation of the guide sheath, especially at the distal end, can interfere with the precise positioning of an implant at the treatment site. Thus, a need exists for improved steerable shaft devices.

SUMMARY

Certain embodiments of the disclosure concern delivery apparatuses with steerable shafts. In a representative embodiment, a delivery apparatus comprises a steerable shaft having a proximal portion, a distal portion, and a pull-wire conduit that extends at least partially through the proximal and distal portions of the shaft. The delivery apparatus further includes a pull wire extending through the pull-wire conduit and having a proximal end portion and a distal end portion. The distal end portion of the pull wire is fixed to the distal portion of the shaft. The delivery apparatus further comprises an adjustment mechanism operatively connected to the proximal end portion of the pull wire and configured to increase and decrease tension in the pull wire to adjust the curvature of the distal portion of the shaft. The distal portion of the shaft comprises a steerable portion having one or more layers. The steerable portion includes a compression-resistance portion incorporated into a respective layer of the steerable portion, and extending angularly along a portion of a cross-section of the layer. The layer of the steerable portion into which the compression-resistance portion is incorporated has a first hardness, and the compression-resistance portion has a second hardness that is greater than the first hardness.

In another representative embodiment, a method comprises inserting a shaft of a delivery apparatus into the body of a patient, the shaft having a proximal portion, a distal portion, and a pull-wire conduit that extends at least partially through the proximal and distal portions. A pull wire extends through the pull-wire conduit, and the distal portion of the shaft comprises a steerable portion having one or more layers. The steerable portion includes a compression-resistance portion incorporated into a respective layer of the steerable portion and extending angularly along a portion of a cross-section of the layer. The layer of the steerable portion into which the compression-resistance portion is incorporated has a first hardness, and the compression-resistance portion has a second hardness that is greater than the first hardness. The method further comprises applying tension to the pull wire to adjust the curvature of the distal portion of the shaft.

In another representative embodiment, a delivery apparatus comprises a steerable shaft having a proximal portion, a distal portion, and a pull-wire conduit that extends at least partially through the proximal and distal portions of the shaft. The delivery apparatus further includes a pull wire extending through the pull-wire conduit and having a proximal end portion and a distal end portion. The distal end portion of the pull wire is fixed to the distal portion of the shaft. The delivery apparatus further comprises an adjustment mechanism operatively connected to the proximal end portion of the pull wire and configured to increase and decrease tension in the pull wire to adjust the curvature of the distal portion of the shaft. The distal portion of the shaft comprises one or more layers and a compression-resistance portion incorporated into a respective layer of the distal portion. The compression-resistance portion extends angularly along a portion of a cross-section of the layer and has a hardness that is greater than a hardness of the layer into which the compression-resistance portion is incorporated.

The compression-resistance portion is angularly offset from the pull-wire conduit along the cross-section of the layer.

The foregoing and other objects, features, and advantages of the disclosed technology will become more apparent from the following detailed description, which proceeds with reference to the accompanying figures.

BRIEF DESCRIPTION OF THE DRAWINGS

FIG. 1 is a perspective view of a representative embodiment of a delivery apparatus.

FIG. 2 is a side elevation view of the guide sheath of the delivery apparatus of FIG. 1.

FIG. 3 is cross-sectional side elevation view of the distal portion of the guide sheath of FIG. 1 illustrating the atraumatic tip portion and the coupling portion.

DETAILED DESCRIPTION

Figure 4:
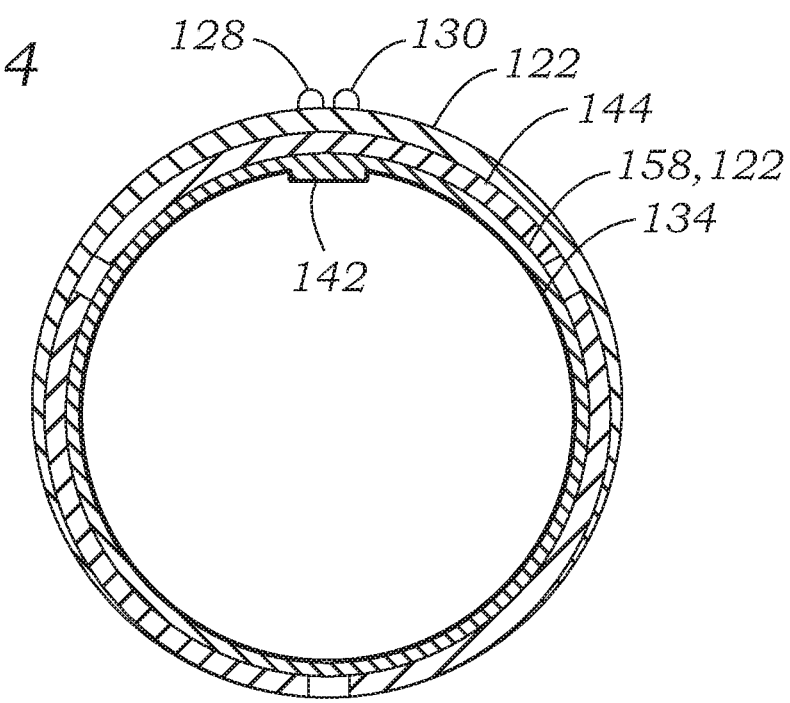
FIG. 4 is a cross-sectional view of the guide sheath of FIG. 1 taken along line 4-4 of FIG. 2.

In particular embodiments, a delivery apparatus that can be used to deliver a medical device, tools, agents, or other therapy to a location within the body of a subject can include one or more steerable catheters or sheaths. Examples of procedures in which steerable catheters and sheaths are useful include neurological, urological, gynecological, fertility (e.g., in vitro fertilization, artificial insemination), laparoscopic, arthroscopic, transesophageal, transvaginal, transvesical, transrectal, and procedures including access in any body duct or cavity. Particular examples include placing implants, including stents, grafts, embolic coils, and the like; positioning imaging devices or components thereof, including ultrasound transducers; and positioning energy sources, for example, for performing lithotripsy, RF sources, ultrasound emitters, electromagnetic sources, laser sources, thermal sources, and the like.

In some embodiments, the delivery apparatus includes a steerable shaft such as a guide sheath having one or more delivery catheters coaxially disposed within the guide sheath. In certain configurations, the delivery catheters can comprise one or more balloons at or near a distal end portion of the catheter. In some implementations, the delivery apparatus can be used to deliver a medical device through the vasculature, such as to a heart of the subject. These devices may comprise one or more eccentrically positioned pull wires configured to cause the steerable shaft to curve in a given direction, or to straighten. The steerable shaft can further comprise a steerable portion located near the distal end of the shaft including a compression-resistance portion that reduces foreshortening of the shaft and increases the degree of curvature attainable for a given pulling force applied to the shaft by the pull wires, thereby enhancing the steerability of the delivery apparatus.

FIG. 1 illustrates a representative embodiment of a delivery apparatus 100 including a handle portion 102 and a shaft configured as a steerable guide sheath 104. The delivery apparatus 100 can be used to perform any diagnostic, therapeutic, or interventional procedure where access to a target location inside the body of a patient is desired. For example, the delivery apparatus 100 can be used to deliver and deploy a prosthetic device in the body, to deliver tools to a target location in the body, or to deliver or introduce drugs or other agents, to name a few exemplary uses.

In certain embodiments, the delivery apparatus can include one or more catheters coaxially disposed within and movable relative to the guide sheath 104. For example, in the illustrated configuration, the delivery apparatus includes an intermediate catheter configured as a steerable catheter 106 disposed within the guide sheath 104, and an inner catheter configured as a delivery or implant catheter 108 coaxially disposed within the steerable catheter 106. The implant catheter 108 can have a prosthetic device 110 mounted on a distal end of the implant catheter in a radially compressed state. In the illustrated configuration, the prosthetic device 110 is a prosthetic heart valve mounted on an inflatable balloon 112 at the distal end of the implant catheter, and the delivery apparatus can be configured to deliver the prosthetic heart valve 110 to one of the native valves of the heart (the aortic, mitral, pulmonary, or tricuspid valves).

In one specific example, the prosthetic heart valve 110 can be a plastically-expandable prosthetic heart valve, and the inflatable balloon 112 can be configured to expand and deploy the valve 110 at a treatment site. Exemplary configurations of the balloon 112 and implant catheter 108 are further disclosed in U.S. Patent Application Publication Nos. 2013/0030519, 2009/0281619, 2008/0065011, and 2007/0005131, the disclosures of which are incorporated herein by reference in their entireties. Exemplary plastically-expandable prosthetic heart valves are disclosed in U.S. Patent Application Publication Nos. 2010/0036484 and 2012/0123529, which are incorporated herein by reference.

In another example, the delivery apparatus 100 can be used to deliver and deploy a self-expandable prosthetic heart valve (e.g., a prosthetic valve having a frame formed from a shape-memory material, such as nitinol). To deliver a self-expandable prosthetic valve, the prosthetic valve can be loaded into a delivery sheath or sleeve in a radially compressed state and advanced from the distal open end of the sheath at the target location to allow the prosthetic valve to expand to its functional size. The delivery sheath can be the distal end portion of the implant catheter 108, or the distal end portion of another shaft that extends through the guide sheath 104. Further details regarding a self-expandable prosthetic valve and delivery devices for a self-expandable prosthetic valve are disclosed in U.S. Patent Application Publication Nos. 2010/0049313 and 2012/0239142, which are incorporated herein by reference. Additionally, it should be understood that the delivery apparatus 100 can be used to deliver any of various other implantable devices, such as docking devices, leaflet clips, etc.

Referring to FIGS. 1 and 2, the steerable guide sheath 104 can include a proximal portion 114 coupled to the handle portion 102, and a distal portion 116. The distal portion 116 can include low durometer atraumatic tip portion 118 coupled to a coupling portion 120 positioned proximally of the atraumatic tip 118. In certain configurations, the atraumatic tip 118 can be radiopaque. The distal portion 114 of the guide sheath 104 can include a steerable portion 122 located proximally of the coupling portion 120 and configured to flex and unflex to adjust the curvature of the distal portion of the guide sheath, as described in detail below.

FIGS. 3-10 illustrate the construction of the guide sheath 104, and particularly of the distal portion 116, in greater detail. The curvature of the guide sheath 104 can be controlled by one or more eccentrically-positioned pull wires (see, e.g., FIGS. 3, 5, and 8). For example, in the illustrated configuration the guide sheath 104 includes two pull wires 124, 126 extending longitudinally through respective pull-wire lumens or conduits 128, 130. The assembled pull wires 124, 126 and conduits 128, 130 can be disposed in a pull-wire conduit portion 154 of the guide sheath. In the illustrated configuration, the pull-wire conduit portion 154 is at least partially defined by a recess 142 of an inner layer 134 of the guide sheath. In the illustrated configuration, the recess 142 can extend into an inner diameter $D_1$ of the guide sheath 104, although other configurations are possible. In certain embodiments, the pull-wire conduits 128, 130 can be made from a lubricious material, such as polytetrafluoroethylene (PTFE) to reduce friction between the pull wires 124, 126 and the respective conduits 128, 130 as the pull wires move within the conduits.

The pull wires 124, 126 can be coupled at one end to a pull ring 144 embedded in the coupling portion 120, and coupled at the opposite end to a control mechanism configured as a rotatable knob 132 of the handle 102 (see FIG. 1). Rotation of the knob 132 can increase and decrease tension in the pull wires 124, 126 which, in turn, can cause the distal portion 116, and particularly the steerable portion 122, to flex and unflex to control the curvature of the guide sheath. A cross-sectional view of the coupling portion 122 illustrating the pull ring 144 encapsulated in the coupling portion is shown in FIG. 4.

Figure 5:
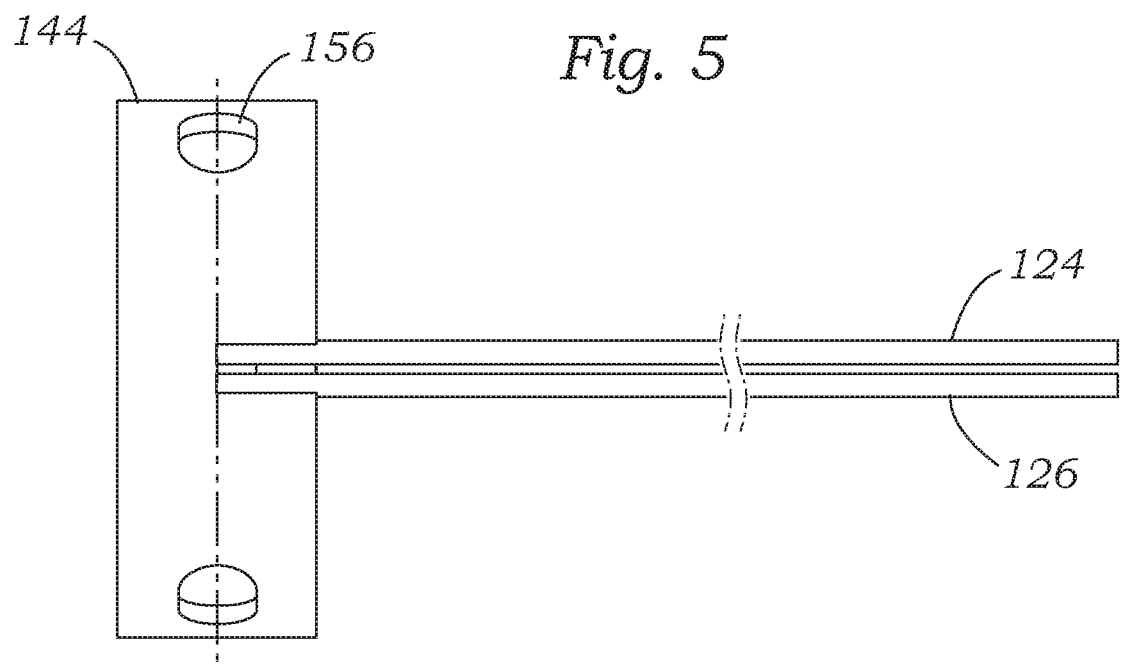
FIG. 5 is a side elevation view illustrating the pull ring and the distal portions of the pull wires coupled to the pull ring.
Figure 12:
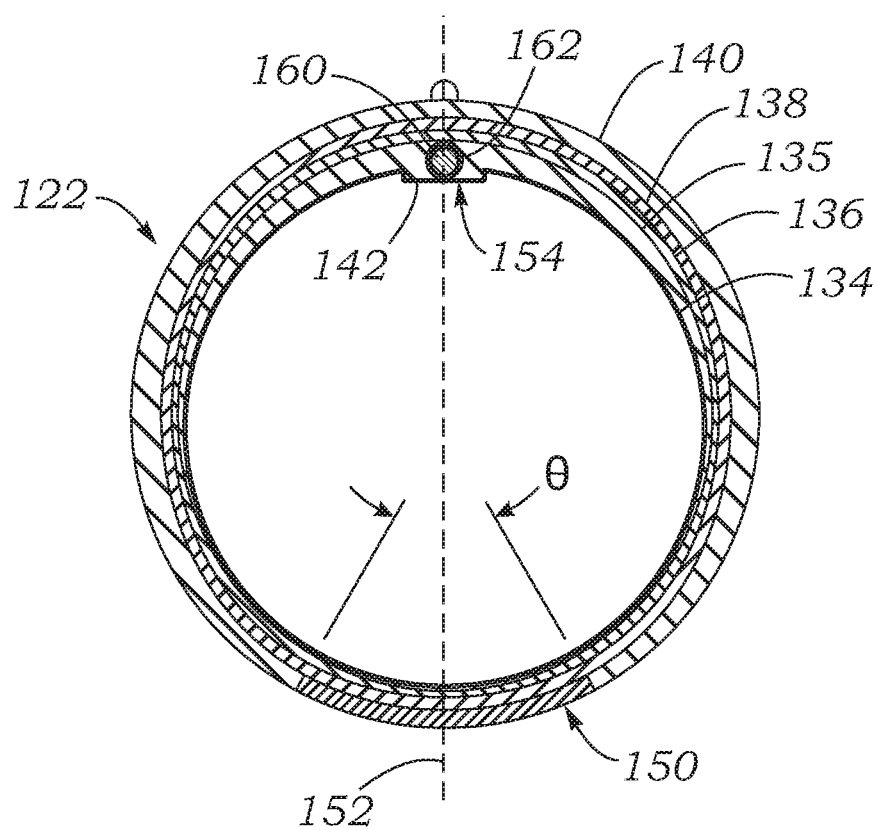
FIG. 12 is a cross-sectional view of an alternative embodiment of a guide sheath including one pull wire.

The pull ring 144 and the distal portions of the pull wires 124, 126 are shown in isolation in FIG. 5. In the illustrated configuration, the pull ring 144 can define a plurality of openings 156 about its circumference. During fabrication of the guide sheath 104, the polymeric material of the coupling portion 120 can be reflowed over the pull ring 144, and the material can flow through the openings 156 to encapsulate the pull ring in the coupling portion, as shown in FIG. 3. Additionally, although the illustrated embodiment includes two pull wires 124, 126, it should be understood that other configurations are possible. For example, the guide sheath 104 can include any suitable number of pull wires having any suitable size or layout, including a single pull wire (see FIG. 12), or more than two pull wires, depending upon the requirements of the device. The particular embodiment illustrated herein includes two pull wires because, in some configurations, two pull wires can occupy a smaller cross-sectional area than that of a single larger pull wire for transmitting a given force to the pull ring 144, particularly when relatively large forces are required (such as when flexing the guide sheath loaded with the steerable catheter 106 and the implant catheter 108).

Figure 6:
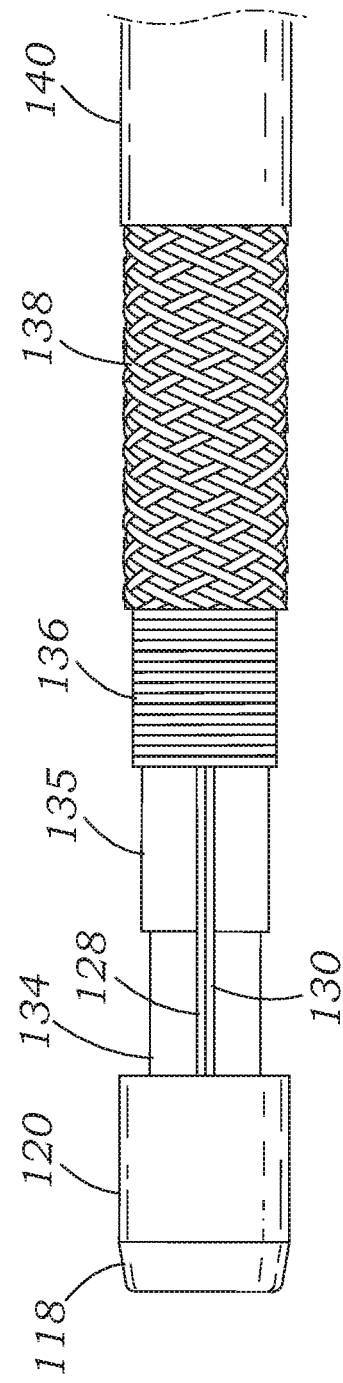
FIG. 6 is a plan view of the distal portion of the guide sheath of FIG. 1 illustrating the various layers of the guide sheath.

Referring to FIGS. 3-10, the guide sheath 104 can include a plurality of layers comprising a variety of different materials at different locations along the length of the guide sheath and configured to impart various properties to the guide sheath. For example, with reference to FIGS. 3 and 6, the steerable portion 122 of the guide sheath 104 comprises a first inner layer 134 defining an inner diameter $D_1$ of the guide sheath 104, and a second pull-wire conduit encapsulating layer 135 disposed radially outward of the inner layer 134. A third helically coiled layer 136 extends over the pull-wire conduit encapsulating layer 135. A fourth braided layer 138 is disposed over the helically coiled layer 136, and a fifth outer layer 140 is disposed over the braided layer, and defines an outer diameter $D_2$ of the guide sheath. FIG. 6 illustrates a plan view of the distal portion 116 of the guide sheath 104 with each of the outer layer 140, the braided layer 138, the helically coiled layer 136, and the pull-wire conduit encapsulating layer 135 shown partially removed to illustrate the construction of the guide sheath.

The first layer 134 extends along the full length of the guide sheath 104, and can be made from (or coated with) a lubricious material (e.g., PTFE) to allow the steerable intermediate catheter 106 to slide relative to the guide sheath 104 within the guide sheath's lumen. As stated above, the first layer 134 can also define the recess 142 of the pull-wire conduit portion 154 in which the pull wires 124, 126 and conduits 128, 130 are received.

The pull-wire conduit encapsulating layer 135 can be disposed between the first inner layer 134 and the helically coiled layer 136, and can have a thickness that varies angularly around the circumference of the guide sheath. For example, with reference to FIGS. 8 and 9, the portion of the pull-wire conduit encapsulating layer 135 proximate the pull-wire conduit portion 154 can be sufficiently thick such that the layer 135 encapsulates the pull-wire conduits 128, 130 in the pull-wire conduit portion. Meanwhile, the portion of the pull-wire conduit encapsulating layer 135 opposite the pull-wire conduit portion 154 can be relatively thin. Alternatively, the pull-wire conduit encapsulating layer 135 can extend around only a portion of the cross-section of the guide sheath, such as around the portion (e.g., half) including the pull-wire conduits 128, 130. In such a configuration, the helically coiled layer 136 can directly contact the inner layer 134 along the portion of the inner layer's cross-section that is opposite the pull-wire conduits, and can transition over the pull-wire conduit encapsulating layer 135 at the location along the circumference of the inner layer 134 where the pull-wire conduit encapsulating layer originates. In some embodiments, the pull-wire conduit encapsulating layer 135 can be made from any suitable polymer, such as any of various polyether block amides (e.g., Pebax®). In certain configurations, the pull-wire conduit encapsulating layer 135 can extend from the proximal end of the coupling portion 120, through the steerable portion 122, to the pull wire exit 148 (FIG. 2).

The helically coiled layer 136 can be formed from, for example, a wire helically wrapped or wound about the pull-wire conduit encapsulating layer 135 or the first layer 134. In the illustrated embodiment, the helically coiled layer 136 can extend from adjacent the pull ring 144 proximally through the coupling portion 120 and the steerable portion 122 to a transition region 146 (FIG. 1) located between the proximal and distal portions 114, 116. In certain embodiments, the transition region 146 where the helically coiled layer 136 ends can be the location at which the outer layer 140 changes from a material having a relatively higher durometer or hardness (e.g., 63D Pebax®) to a material having a relatively lower durometer (e.g., a polyamide such as VESTAMID®). In some embodiments, gradually varying (e.g., stepwise) the hardness of the outer layer 140 or the other layers of the shaft along their length can reduce the likelihood of kinking, fracture, or warping of the shaft during flexing, or when traversing vessels of the body. Additionally, in certain examples, the helically coiled layer 136 can be made from stainless steel or titanium flat wire wound at, for example, 50 coils per inch with a pitch of 0.020 inch, and can be configured to resist kinking or crushing of the guide shaft 104, and particularly of the steerable portion 122, when it is flexed.

The braided layer 138 can extend over the helically coiled layer 136. In the illustrated configuration, the braided layer 138 can extend from the coupling portion 120 proximate the pull ring 144 proximally to, for example, the pull wire exit 148. The braided layer 138 can be, for example, metal wires braided together in a pattern to form a tubular layer over the helically coiled layer 136. For example, in the illustrated embodiment the braided layer 138 is made from stainless steel or titanium flat wires braided in an over 1 under 1 pattern, although any suitable braid pattern can be used. For example, in another representative embodiment, the wires of the braided layer 138 can be braided in a 1 over 2, under 2 pattern with a pick count of 60 picks per inch (PPI). The braided layer 138 can be configured to, for example, resist undesirable torsional deformation of the guide sheath 104 to allow the guide sheath to transmit torque, which can aid in positioning the implant at the treatment site. The braided layer 138 can also provide crush or kink-resistance properties to the guide sheath 104. In the illustrated configuration, the coupling portion 120 can also include a braided layer 158 disposed beneath the pull ring 144, as shown in FIGS. 3 and 4.

Figure 10:
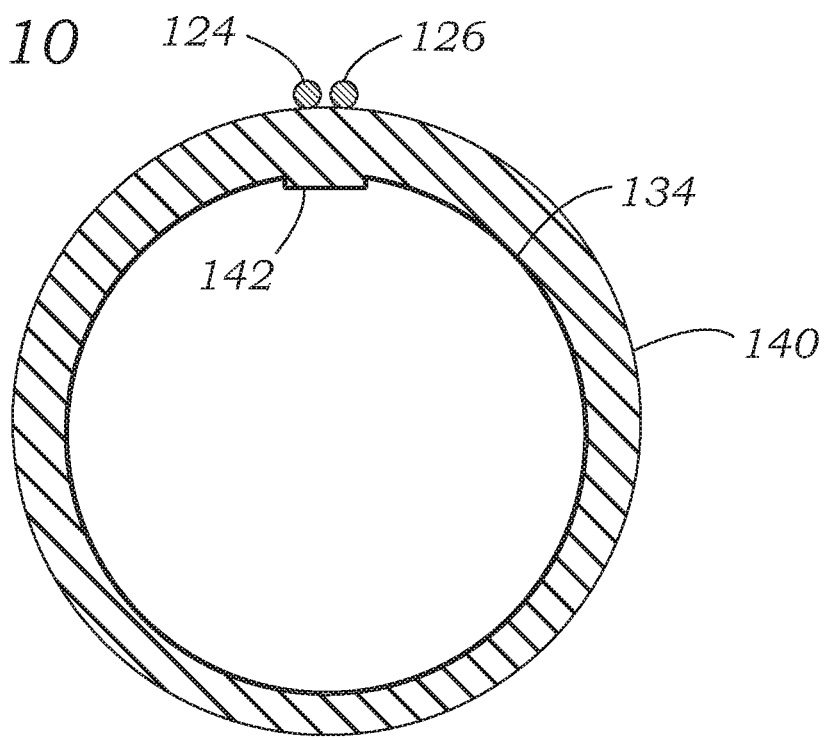
FIG. 10 is a cross-sectional view of the guide sheath of FIG. 1 taken along line 10-10 of FIG. 2.

The outer layer 140 can comprise, for example, any of a variety of polymeric materials such as polyamides (e.g., VESTAMID®), polyether block amides (e.g., Pebax®), nylon, or any other suitable biocompatible polymer or combinations thereof along its length. In the illustrated configuration, the pull-wire conduit encapsulating layer 135, the helically coiled layer 136, and the braided layer 138 can terminate distally of the proximal end of the guide sheath 104. For example, in some configurations these layers can terminate at the pull wire exit 148. Proximally of the pull wire exit 148, the outer layer 140 can increase in thickness to maintain a substantially uniform outer diameter along the length of the guide sheath, as illustrated in FIG. 10.

Figure 7:
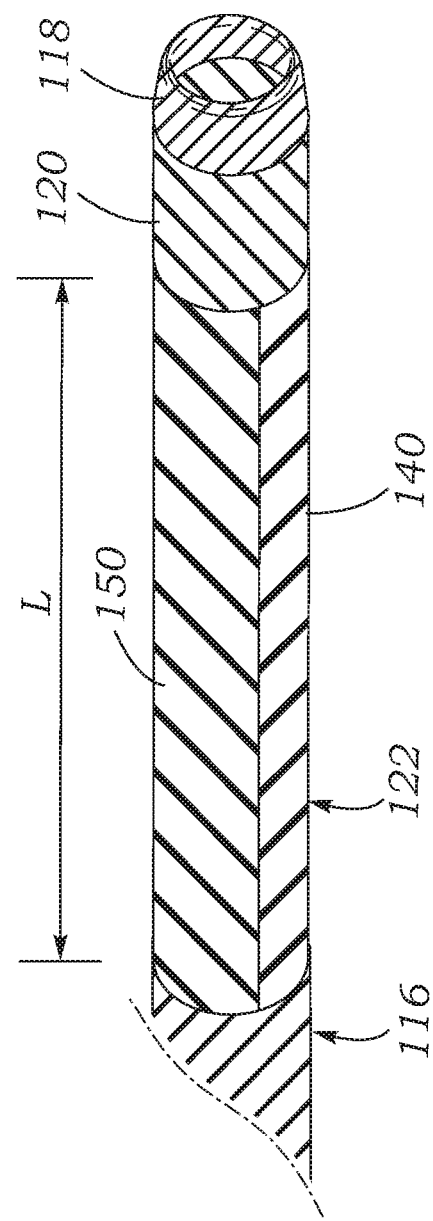
FIG. 7 is a perspective view of the distal portion of the guide sheath of FIG. 1 illustrating the compression-resistance portion of the outer layer.
Figure 8:
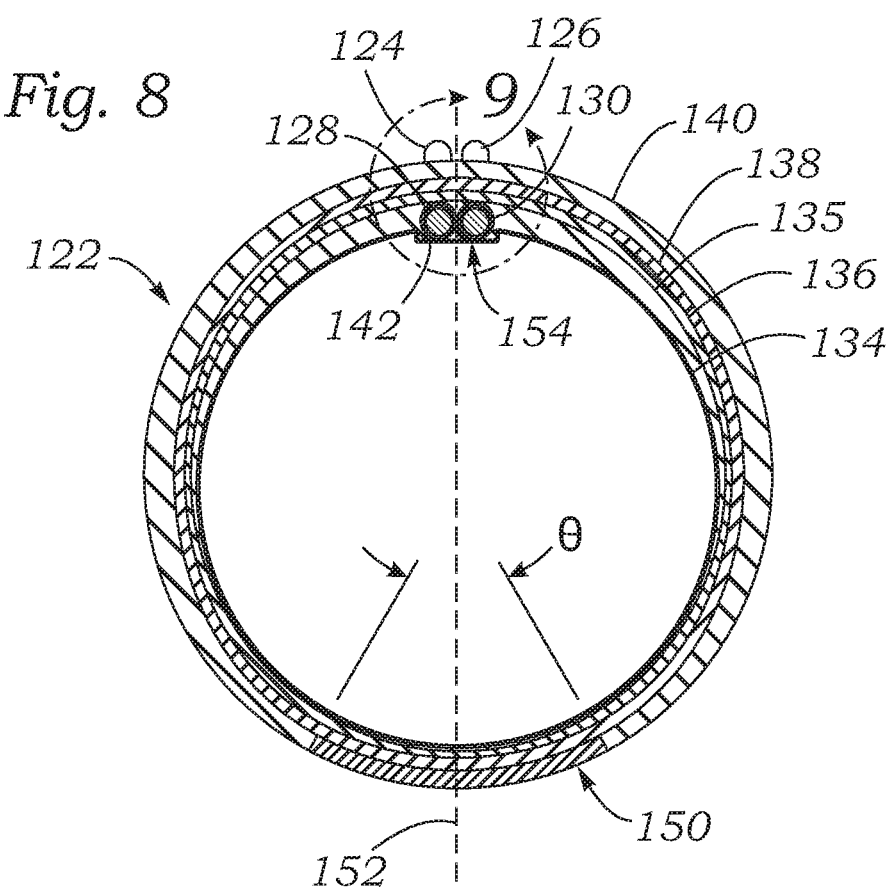
FIG. 8 is a cross-sectional view of the guide sheath of FIG. 1 taken along line 8-8 of FIG. 2.
Figure 9:
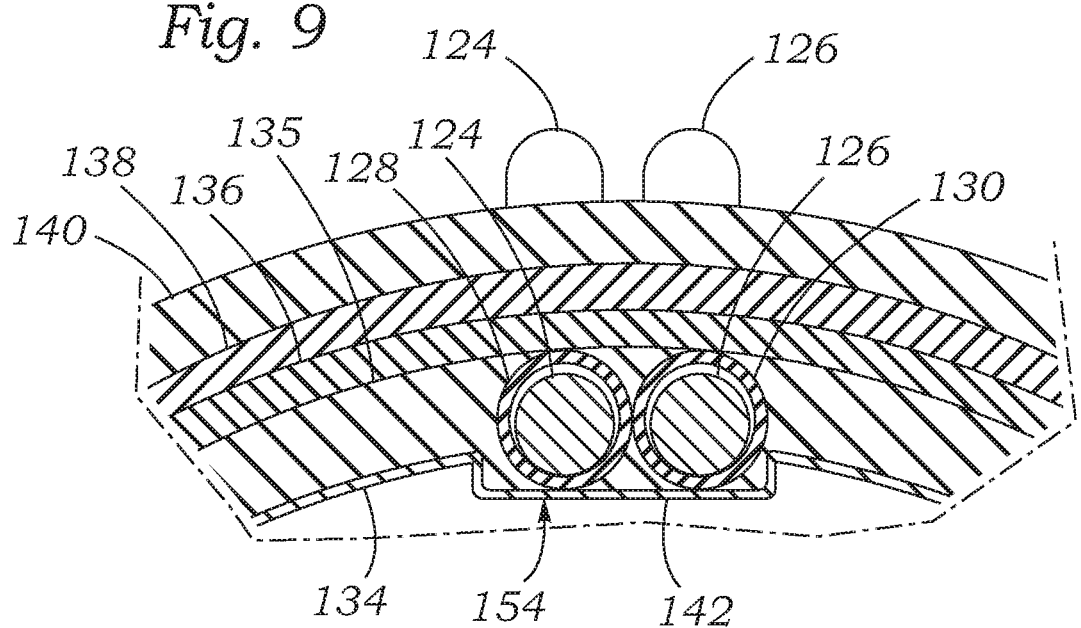
FIG. 9 is a detail view of the pull-wire conduit receiving portion of the guide sheath of FIG. 8.

Referring to FIGS. 7 and 8, the distal portion 116 of the guide sheath 104 can include a compression-resistance portion 150. In the illustrated configuration, the compression-resistance portion 150 is incorporated into the outer layer 140, and forms a respective part of the steerable section 122. As illustrated in FIG. 7, the compression-resistance portion 150 can extend along a length L of the steerable portion 122. The compression-resistance portion 150 can also extend circumferentially or angularly along, or occupy a respective portion of, the cross-section of the outer layer 140. For example, with reference to FIG. 8, the angular extent of the compression-resistance portion 150 along the cross-section of the outer layer 140 is denoted by the angle θ. In some embodiments, the angle θ can be from 10 degrees to 180 degrees (or half of the circumference of the cross-section). In some embodiments, the angle θ can be from 10 degrees to 90 degrees. In the embodiment of FIG. 8, the angle θ is 60 degrees.

In certain configurations, the compression-resistance portion 150 can be disposed opposite the pull wire conduits 128, 130. For example, in the illustrated configuration, the compression-resistance portion 150 is angularly offset from the pull wire conduit portion 154 by 180 degrees such that it is located diametrically opposite the pull wire conduits 128, 130. In this configuration, a plane 152 that bisects the pull wire conduit portion 154 also bisects the compression-resistance portion 150, as shown in FIG. 8. In the configuration of FIG. 8 including two pull wires and conduits, the plane 152 bisecting the pull-wire conduit portion 154 passes between the respective conduits 128, 130. However, in configurations including a single pull wire, such as the alternative configuration illustrated in FIG. 12, a single pull wire 160 and conduit 162 can be coaxially aligned with the pull-wire conduit portion 154 such that the plane 152 bisecting the pull-wire conduit portion 154 and the compression-resistance portion 150 also bisects the pull wire 160 and the conduit 162. In other configurations, the compression-resistance portion 150 can be angularly offset from the pull-wire conduit portion 154 along the cross-section of the outer layer 140 by, for example, from 90 degrees to 180 degrees, as desired.

The compression-resistance portion 150 can be made from a material having a relatively higher hardness or durometer than the remainder of the outer layer 140 in the steerable portion 122 in which the compression-resistance portion is incorporated. For example, in certain embodiments the compression-resistance portion 150 can have a durometer that is from 1.5 times to 5 times greater than a durometer of the remainder of the outer layer 140 in the steerable portion 122. In some embodiments, the durometer of the compression-resistance portion 150 can be from 2 times to 3 times greater than the durometer of the remainder of the outer layer 140 in the steerable portion 122. In an exemplary embodiment, the compression-resistance portion 150 can be made from PEBAX® having a durometer of 72D, and the remainder of the outer layer 140 of the steerable portion 122 can be made from PEBAX® having a durometer of 25D, such that a ratio of the durometer of the compression-resistance portion 150 and the durometer of the remainder of the outer layer 140 in the steerable portion 122 is 2.9:1. In some embodiments, the ratio of the durometer of the compression-resistance portion 150 to the durometer of the remainder of the outer layer 140 in the steerable portion 122 can be 3:1.

In other embodiments, the compression-resistance portion 150 can be made of any of various materials exhibiting suitable hardness properties, including metals such as stainless steel, titanium, nickel titanium alloys such as nitinol, cobalt chromium, or other polymers. In addition, in certain configurations, the compression-resistance portion need not have a thickness equal to the overall thickness of the outer layer 140. For example, the compression-resistance portion 150 can have a thickness that is less than the overall thickness of the outer layer, and may be encapsulated within the outer layer, as desired. The durometer of the compression-resistance portion 150 can also vary along its length. For example, the proximal portion of the compression-resistance portion 150 can have a relatively lower durometer than the distal portion, or vice versa.

The compression-resistance portion 150 can provide a variety of advantageous characteristics to the steerable portion 122 of the guide sheath 104. For example, the relatively higher durometer of the compression-resistance portion 150 can provide axial strength to the steerable portion 122. This can significantly reduce or prevent undesirable foreshortening of the guide sheath 104, and particularly of the steerable portion 122, when the guide catheter is flexed. More particularly, the compression-resistance portion 150 can reduce axial compression of the guide sheath and associated wrinkling of the material when the guide sheath is flexed compared to when it is in a non-deflected state. Such axial compression and wrinkling of the material can decrease the length of the guide sheath 104 as the material is deformed, and can damage the guide sheath. By reducing or eliminating foreshortening of the guide sheath 104 when it is flexed, the compression-resistance portion 150 can reduce the need for the operator to longitudinally reposition the delivery apparatus (e.g., by advancing or retracting the delivery apparatus through the patient's vasculature) in order to obtain or regain a desired position of the implant at the treatment site after flexing the guide sheath.

Figure 11:
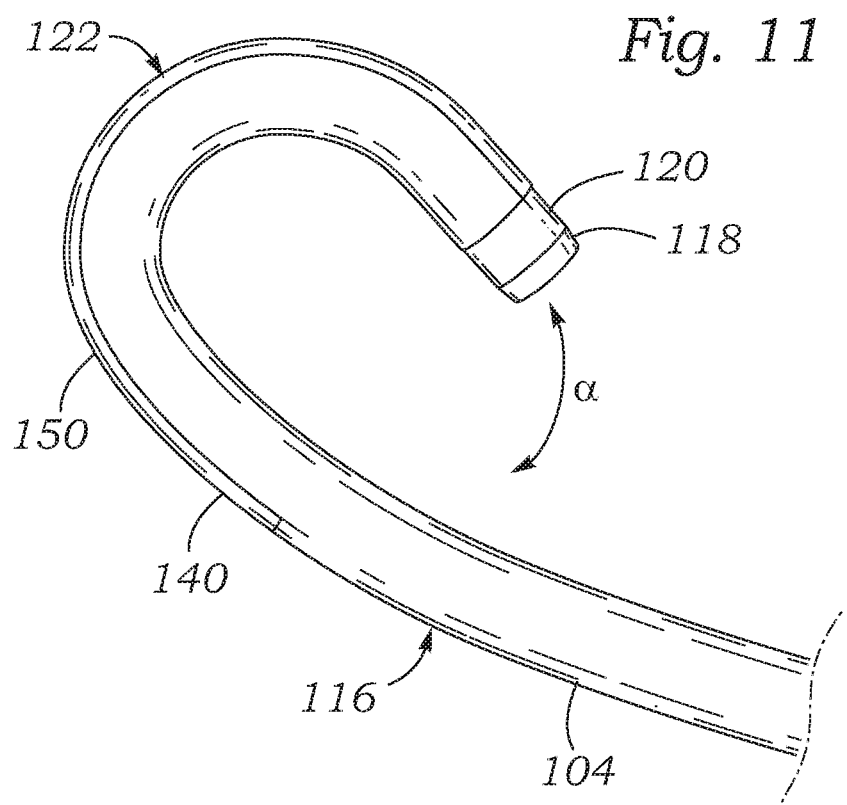
FIG. 11 is a perspective view of the guide sheath of FIG. 1 illustrating flexing of the guide sheath.

Additionally, the location of the compression-resistance portion 150 angularly offset from the pull wire conduits 128, 130 can aid in initiating deformation of the steerable portion 122 of the guide sheath in a specified direction. For example, when the compression-resistance portion 150 is located opposite the pull wire conduits 128, 130, the axial stiffness of the compression-resistance portion can induce deflection of the steerable portion 122 in a direction away from the compression-resistance portion when the guide sheath is flexed, as illustrated in FIG. 11. The compression-resistance portion 150 can also reduce or prevent ovalizing (also referred to as "pancaking") of the guide sheath by reducing longitudinal movement of the different layers of the sheath relative to one another when the sheath is flexed, especially in cases in which one or more constituent layers (e.g., PTFE layers such as inner layer 134) are not strongly adhered to the surrounding layer(s).

The compression-resistance portion 150 can also increase the degree of flexion of the distal portion 116 attainable for a given force applied to the distal portion by the pull wires 124, 126, without damaging the guide sheath. The angle of flexion of the distal portion 116 is denoted a, and is illustrated in FIG. 11. For example, by reducing foreshortening of the guide sheath 104, a greater proportion of the force applied by the pull wires 124, 126 is available to flex the guide sheath instead of elastically compressing the guide sheath. Additionally, the compression-resistance portion 150 can reduce or prevent slackening of the pull wires 124, 126 attendant to foreshortening of the guide sheath 104 when it is flexed, resulting in a greater degree of curvature attainable for a given pull wire travel as compared to typical guide sheaths. As used herein, the term "pull wire travel" refers to the linear distance that a given point along the length of a pull wire moves with respect to a stationary reference (e.g., a pull wire conduit) when tension is applied to the pull wire.

Additionally, the compression-resistance portion 150, together with the helically coiled layer 136, and the braided layer 138 described above, can provide significant synergistic advantages that improve the performance of the guide sheath 104 over known steerable sheaths and catheters. For example, the distal portion of an unloaded guide sheath (e.g., a guide sheath without a delivery catheter or other shaft extending through its lumen) having an inner diameter of 22 Fr and including the compression-resistance portion, helically coiled layer, and braided layer features is capable of flexing nearly 355 degrees without kinking, and without significant foreshortening, under a force of 175 N applied by the pull wires. In this example, 50 mm of pull wire travel were required to apply a force of 175 N to the distal portion of the guide sheath. In contrast, for a typical steerable catheter device without the compression-resistance portion and without a delivery catheter or other sheath extending through its lumen, a force of 175 N produces 270 degrees of flexure and requires 60 mm of pull wire travel, and the guide sheath can be expected to foreshorten by 6 mm to 10 mm.

In another example, the distal portion of a guide sheath having an inner diameter of 22 Fr and including the above compression-resistance portion, helically coiled layer, and braided layer features, and loaded with a delivery catheter and an implant catheter extending coaxially within the lumen of the guide sheath, was capable of flexing 270 degrees without kinking, and without significant foreshortening, under a force of 250 N applied by the pull wires. In this example, 40 mm of pull wire travel were required to apply a force of 250 N to the distal portion of the guide sheath. In contrast, for a steerable catheter device without the compression-resistance portion and loaded with a delivery catheter and an implant catheter, a force of 250 N produces 180 degrees of flexure and requires 70 mm of pull wire travel, and the guide sheath can be expected to foreshorten by 6 mm to 10 mm.

In use, the delivery apparatus 100 can be introduced and advanced through the patient's vasculature using any known delivery technique. In a transfemoral procedure, the delivery apparatus can be inserted through a femoral artery and the aorta to access the heart (typically, but not exclusively used for aortic valve replacement). In a transeptal procedure (typically used for aortic or mitral valve replacement), the delivery device can be advanced to the right atrium, such as via a femoral vein, and through the septum separating the right and left ventricles. The disclosed embodiments can be particularly useful for delivering a prosthetic valve to the native mitral valve, as the torqueability of the guide sheath 104 and the relatively high degree of curvature achievable with the distal portion 116 allows for precise positioning of the prosthetic valve at the target site despite the tortuous pathway the delivery apparatus must follow to access the mitral valve in some approaches. In a transventricular procedure, the delivery apparatus can be inserted through a surgical incision made on the bare spot on the lower anterior ventricle wall (typically, but not exclusively used for aortic or mitral valve replacement). In a transatrial procedure, the delivery apparatus can be inserted through a surgical incision made in the wall of the left or right atrium. In a transaortic procedure, the delivery apparatus can be inserted through a surgical incision made in the ascending aorta and advanced toward the heart (typically, but not exclusively used for aortic valve replacement).

In certain of these procedures, the combination of the compression-resistance portion 150, the helically coiled layer 136, and the braided layer 138 can aid in precisely positioning a prosthetic device, such as the heart valve 110, at a treatment site. For example, in a transseptal procedure to access the mitral valve, after the distal end of the delivery apparatus is advanced to the treatment site, the distal portion 116 of the guide sheath 104 can be flexed to axially align the prosthetic valve 110 with the mitral valve (e.g., 180 degrees or more, in certain examples). While the distal portion 116 is in a flexed state, the guide sheath 104 can also be torqued to radially position the prosthetic valve 110 with respect to the mitral valve. The combination of the compression-resistance portion 150, the helically coiled layer 136, and the braided layer 138 can allow the guide sheath to flex without significant foreshortening or kinking, and to be torqued without undesirable torsional deformation of the shaft or associated unpredictable rotational motion of the guide sheath.

It should be understood that in alternative configurations, the components of the disclosed delivery apparatus embodiments can be rearranged without departing from the spirit of the disclosure. For example, the locations of the helically coiled layer 136 and the braided layer 138 can be reversed such that the helically coiled layer is on top of the braided layer. Alternatively, the helically coiled layer 136 and the braided layer 138 can be separated from one another by one or more intermediate layers. Additionally, the compression-resistance portion 150 need not be a respective portion of the outer layer 140, but can be incorporated into any suitable layer in the guide sheath 104. The compression-resistance portion 150 also need not extend along the entire length of the steerable portion 122, but can extend along any suitable portion of the steerable portion. The disclosed compression-resistance portion, helically coiled layer, and braided layer features described herein can also be applicable to other types of steerable catheter devices, such as delivery catheters.

GENERAL CONSIDERATIONS

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

Unless otherwise indicated, all numbers expressing quantities of components, distances, forces, ratios, angles, percentages, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

What is claimed is:

1. A delivery apparatus, comprising:
a steerable shaft having a pull-wire conduit;
a pull wire extending through the pull-wire conduit;
wherein the steerable shaft has one or more layers;
wherein the steerable shaft includes a compression-resistance portion incorporated into at least one of the one or more layers of the steerable shaft;
wherein a cross-section of the compression-resistance portion has an arcuate shape that extends along a portion of a cross-section of the steerable shaft;
wherein the compression-resistance portion has a hardness that is greater than a hardness of the one or more layers that the compression-resistance portion is incorporated into;
wherein the steerable shaft comprises a first inner layer that defines an inner diameter of the shaft and a second outer layer that defines an outer diameter of the shaft; and
wherein the compression-resistance portion is incorporated into the second outer layer of the shaft.

2. The delivery apparatus of claim 1, further comprising an adjustment mechanism operatively connected to a proximal end portion of the pull wire and configured to increase and decrease tension in the pull wire to adjust the curvature of a distal portion of the steerable shaft.

3. The delivery apparatus of claim 1, wherein the compression-resistance portion is located opposite the pull-wire conduit.

4. The delivery apparatus of claim 1, wherein the compression-resistance portion extends from 10 degrees to 180 degrees along the cross-section of the steerable shaft.

5. The delivery apparatus of claim 4, wherein the compression-resistance portion extends about 60 degrees along the cross-section of the steerable shaft.

6. The delivery apparatus of claim 1, wherein the steerable shaft further comprises a third helically coiled layer between the inner layer and the outer layer.

7. The delivery apparatus of claim 6, wherein the steerable shaft further comprises a fourth braided layer braided over at least a portion of the third helically coiled layer.

8. The delivery apparatus of claim 7, wherein the steerable shaft further comprises a pull-wire conduit encapsulating layer between the first inner layer and the third helically coiled layer that encapsulates the pull-wire conduit.

9. The delivery apparatus of claim 1, wherein the first inner layer defines a recess configured to receive the pull-wire conduit.

10. The delivery apparatus of claim 1, wherein a ratio of the hardness of the compression-resistance portion to the hardness of the second outer layer is from 1.5:1 to 5:1.

11. The delivery apparatus of claim 10, wherein the ratio is 3:1.

12. The delivery apparatus of claim 1, wherein the steerable shaft is a guide sheath, and the delivery apparatus further includes an implant catheter coaxially disposed within the guide sheath including a prosthetic device mounted on a distal end of the implant catheter.

13. The delivery apparatus of claim 1, further comprising a pull ring embedded in a distal portion of the shaft and coupled to a distal end of the pull wire, wherein the compression-resistance portion is proximally spaced apart from the pull ring.

14. The delivery apparatus of claim 1, wherein the first inner layer defines a recess configured to receive the pull-wire conduit at a location radially inward of the second outer layer.

15. A system, comprising:
a steerable guide sheath comprising:
a steerable shaft having a pull-wire conduit;
a pull wire extending through the pull-wire conduit;
wherein the steerable shaft has one or more layers;
wherein the steerable shaft includes a compression-resistance portion incorporated into at least one of the one or more layers of the steerable shaft;
wherein a cross-section of the compression-resistance portion has an arcuate shape that extends along a portion of a cross-section of the steerable shaft; and
wherein the compression-resistance portion has a hardness that is greater than a hardness of the one or more layers that the compression-resistance portion is incorporated into;
an adjustment mechanism connected to a proximal end portion of the guide sheath and configured to increase and decrease tension in the pull wire to adjust the curvature of a distal portion of the steerable guide sheath;
an implant catheter coaxially disposed within the guide sheath; and
a prosthetic device mounted on a distal end of the implant catheter,
wherein the steerable shaft comprises a first inner layer that defines an inner diameter of the shaft and a second outer layer that defines an outer diameter of the shaft; and
wherein the compression-resistance portion is incorporated into the second outer layer of the shaft.

16. The system of claim 15, wherein a ratio of the hardness of the compression-resistance portion to the hardness of second outer layer is from 1.5:1 to 5:1.

17. The system of claim 15, wherein the compression-resistance portion is located opposite the pull-wire conduit.

18. The system of claim 15, wherein the compression-resistance portion extends from 10 degrees to 180 degrees along the cross-section of the steerable shaft.

19. The system of claim 18, wherein the compression-resistance portion extends 60 degrees along the cross-section of the steerable shaft.

20. A delivery apparatus, comprising:
a steerable shaft having a distal portion and a pull-wire conduit;
a pull wire extending through the pull-wire conduit;
a pull ring embedded in the distal portion of the shaft and coupled to a distal end of the pull wire,
wherein the steerable shaft has one or more layers;
wherein the steerable shaft includes a compression-resistance portion proximally spaced apart from the pull ring and incorporated into at least one of the one or more layers of the steerable shaft;
wherein a cross-section of the compression-resistance portion has an arcuate shape that extends along a portion of a cross-section of the steerable shaft; and
wherein the compression-resistance portion has a hardness that is greater than a hardness of the one or more layers that the compression-resistance portion is incorporated into.

21. The delivery apparatus of claim 20, wherein the compression-resistance portion is located opposite the pull-wire conduit.

22. The delivery apparatus of claim 20, wherein the compression-resistance portion extends from 10 degrees to 180 degrees along the cross-section of the steerable shaft.

23. The delivery apparatus of any of claim 20, wherein:
the steerable shaft comprises a first inner layer that defines an inner diameter of the shaft and a second outer layer that defines an outer diameter of the shaft; and
the compression-resistance portion is incorporated into the second outer layer of the shaft.

24. The delivery apparatus of claim 23, wherein the shaft further comprises a third helically coiled layer between the first inner layer and the second outer layer, and a fourth braided layer braided over at least a portion of the third helically coiled layer.

25. The delivery apparatus of claim 23, wherein the first inner layer defines a recess configured to receive the pull-wire conduit at a location radially inward of the second outer layer.

* * * * *